US009034023B2

United States Patent
Kruijt et al.

(10) Patent No.: US 9,034,023 B2
(45) Date of Patent: May 19, 2015

(54) DYNAMIC COLORECTAL PDT APPLICATION

(75) Inventors: Bastiaan Kruijt, Schiedam (NL); Eric M van der Snoek, Rotterdam (NL); Henricus J. C. M. Sterenborg, Capelle aan den Ijssel (NL); Arjen Amelink, Gouda (NL); Dominic J. Robinson, Rotterdam (NL); Wolfgang Neuberger, Dubai (AE)

(73) Assignee: Biolitec Pharma Marketing Ltd, Labuan (MA)

( * ) Notice: Subject to any disclaimer, the term of this patent is extended or adjusted under 35 U.S.C. 154(b) by 1 day.

(21) Appl. No.: 13/357,319

(22) Filed: Jan. 24, 2012

(65) Prior Publication Data

US 2012/0259187 A1 Oct. 11, 2012

Related U.S. Application Data

(60) Provisional application No. 61/435,635, filed on Jan. 24, 2011.

(51) Int. Cl.
*A61N 5/06* (2006.01)
*A61K 31/409* (2006.01)
(Continued)

(52) U.S. Cl.
CPC .............. *A61N 5/062* (2013.01); *A61K 31/409* (2013.01); *A61B 5/0071* (2013.01); *A61B 5/0084* (2013.01);
(Continued)

(58) Field of Classification Search
CPC .... A61B 5/007; A61B 5/0084; A61B 5/4255; A61N 2005/0608; A61N 2005/0628; A61N 2005/063; A61N 2005/0662; A61N 5/062
USPC ........ 600/317, 476–479; 607/74–95; 604/264
See application file for complete search history.

(56) References Cited

U.S. PATENT DOCUMENTS

| 5,707,401 A * | 1/1998 | Talmore ........................ 607/88 |
| 6,986,782 B2 * | 1/2006 | Chen et al. ..................... 607/88 |

(Continued)

FOREIGN PATENT DOCUMENTS

| WO | WO 2005029051 A1 * | 3/2005 |
| WO | WO 2006025940 A2 * | 3/2006 |

(Continued)

OTHER PUBLICATIONS

"Fiber Optic Probes for Biomedical Optical Spectroscopy", Utzinger et al., Biomedical Engineering, The University of Austin, Feb. 2001.*

*Primary Examiner* — Gary Jackson
*Assistant Examiner* — Boniface N. Nganga
(74) *Attorney, Agent, or Firm* — Bulesh J. Skutnik; BJ Associates

(57) ABSTRACT

Dynamic colorectal PDT methods, devices and photosensitizer compositions to treat abnormal cell growth in anal tissue such as perianal and intra-anal intraepithelial neoplasia grade III are presented. Dynamic colorectal PDT method comprises the steps of administering topically, intravenously or orally a photosensitizer composition; irradiating; monitoring treatment parameters before, during and/or after irradiation. Photosensitizer composition comprises Temoporfin and excipients/carriers, appropriate for the application method. An applicator is provided for colorectal PDT treatments enhancing irradiation delivery and monitoring treatment parameters. Preferably, applicator is made of a material, used to monitor the fluence rate simultaneously while doing optical spectroscopy. Measurement probe devices are provided for monitoring PDT treatment parameters in-vivo. A device for colorectal PDT treatment is also provided, comprising laser radiation source operating at about 400 and 800 nm; excitation laser radiation source operating at about 650 nm for fluorescence measurements; multichannel dosimetry device; long pass filter; waveguides and measurement probes.

19 Claims, 5 Drawing Sheets

(51) Int. Cl.
*A61P 35/00* (2006.01)
*A61B 5/02* (2006.01)
*A61M 5/00* (2006.01)
*A61B 6/00* (2006.01)
*A61B 5/1455* (2006.01)
*A61B 5/00* (2006.01)

(52) U.S. Cl.
CPC ....... *A61B 5/4255* (2013.01); *A61N 2005/0608* (2013.01); *A61N 2005/0628* (2013.01); *A61N 2005/063* (2013.01); *A61N 2005/0662* (2013.01)

(56) References Cited

U.S. PATENT DOCUMENTS

| | | | | |
|---|---|---|---|---|
| 8,180,436 | B2 * | 5/2012 | Boyden et al. | 600/476 |
| 8,320,725 | B2 * | 11/2012 | Temelkuran et al. | 385/125 |
| 2003/0232445 | A1 * | 12/2003 | Fulghum, Jr. | 436/63 |
| 2006/0103850 | A1 * | 5/2006 | Alphonse et al. | 356/479 |
| 2006/0155178 | A1 * | 7/2006 | Backman et al. | 600/315 |
| 2006/0282132 | A1 * | 12/2006 | Arai et al. | 607/88 |
| 2007/0282404 | A1 * | 12/2007 | Cottrell et al. | 607/89 |
| 2009/0204009 | A1 * | 8/2009 | Powers et al. | 600/476 |
| 2010/0056927 | A1 * | 3/2010 | Van Gogh et al. | 600/476 |
| 2011/0117025 | A1 * | 5/2011 | Dacosta et al. | 424/9.6 |
| 2012/0100559 | A1 * | 4/2012 | Hell et al. | 435/7.21 |

FOREIGN PATENT DOCUMENTS

| | | | | |
|---|---|---|---|---|
| WO | WO 2008110968 | A1 * | 9/2008 | |
| WO | WO 2008137737 | A2 * | 11/2008 | A61N 5/06 |

* cited by examiner fluorescence differential path length spectroscopy (FDPS) control unit

DYNAMIC COLORECTAL PDT APPLICATION

DOMESTIC PRIORITY UNDER 35 USC 119(E)

This application claims the benefit and priority of U.S. Provisional Application Ser. No. 61/435,635 filed on Jan. 24, 2011, entitled "Dynamic Colorectal PDT Application" by Bastiaan Kruijt, Eric M. van der Snoek, Henricus J. C. M. Sterenborg, Arjen Amelink, Dominic J. Robinson and Wolfgang Neuberger, which is incorporated by reference herein.

BACKGROUND OF THE INVENTION

1. Field of the Invention

The present invention relates to the treatment of abnormal cell growth in the gastrointestinal tract. More particularly, present invention relates to methods, devices and compositions containing hydrophobic photosensitizers for photodynamic therapy for the treatment of unwanted cells and tissues of the intra-anal and perianal region such as anal intraepithelial neoplasia grade III (high grade dysplasia).

2. Invention Disclosure Statement

Anal intraepithelial neoplasia (AIN) or anal dysplasia is an abnormal cell growth in anal tissue that in some cases may progress to cancer. Depending on how the cells look under the microscope, AIN may be further subdivided into AIN Grade I, AIN Grade II and AIN Grade III. The term anal squamous intraepithelial lesions (ASIL) is also used to describe AIN; which can be further classified as low-grade squamous intraepithelial lesions (LSIL) equivalent to AIN I (mild dysplasia), and high-grade squamous intraepithelial lesions (HSIL) which includes AIN II (moderate dysplasia) and AIN III (severe dysplasia). Additionally, the terms anal carcinoma in situ (Stage 0, National Cancer Institute's classification system) and Bowens disease of the anus can also be found in literature, which are sometimes used to denote HSIL. Although LSIL are not thought to be a direct precursor to anal cancer, they may progress to HSIL. On the other hand, HSIL is a progressive, potentially precancerous condition that requires attention; a small proportion of AIN III-type lesions that are not treated or removed may develop into invasive cancer, destroying adjacent tissues and/or organs and ultimately causing death. For this reason it is advantageous to screen for AIN III and treat before it can progress to invasive anal cancer.

To date the management of AIN III lacks accepted treatment protocols. Current treatment modalities for AIN III are electrocautery, cryosurgery and excision but such therapies can result in significant pain or postoperative complications including anal stenosis and severe long-term side effects such as strictures, fecal incontinence and colostomy. Furthermore, ablative treatments are often limited by a high incidence of recurrence. Other treatment options include laser ablation, which can only be used to treat small lesions, and immunomodulation, lacking of sufficient long-term data on therapy results.

In an attempt to provide a method for treating anorectic disorders, Ehrenpreis discloses in U.S. Pat. No. 7,250,445 a method comprising a step of providing a suppository containing between 1000 and 500,000 IU (international units of measure) of an antioxidant selected from the group of Vitamin A, Vitamin C, and Vitamin E; and a step of placing the suppository within rectal cavity for a period of time required for dissolution of the suppository. However, it only provides a substitute or adjunct for conventional treatments for anorectic disorders when no current therapies are available.

Another possible treatment modality, that has the potential for curative treatment of AIN III with less long-term side effects, is PDT. An additional and significant advantage of PDT is that it allows therapeutic illumination of the whole surface of the anal cavity in a single treatment session. This is of importance since other treatment modalities show, based on their high recurrence rates of up to 50%, that it is difficult to determine exactly where to treat for AIN III in the anal cavity.

Photodynamic therapy has been successfully used for superficial, intraluminal and interstitial treatment of (pre) malignant lesions in among others dermatology, esophagus, lungs, head and neck, prostate and vulva. There are a small number of clinical reports on PDT in the anal region for treatment of perianal AIN III and carcinoma in situ using topical or systemic administered ALA. Light delivery for perianal lesions was done using a light delivery device that uses a mirror to direct treatment light onto the treatment area (Hamdan K A, Tait I S, Nadeau V, Padgett M, Carey F, Steele R J; Treatment of grade III anal intraepithelial neoplasia with photodynamic therapy: report of a case; *Dis Colon Rectum.;* 2003; 46:1555-9). For intra-anal treatment of carcinoma in situ a rectal speculum was used to expose the mucosa. Subsequently a linear diffuser was placed in the center of the speculum for therapeutic illumination. Since the speculum shields half of the tissue two illuminations are necessary where for the second illumination the speculum is rotated 90 degrees (Webber J, Fromm D; Photodynamic therapy for carcinoma in situ of the anus; *Arch Surg.;* 2004; 139:259-61).

Unfortunately, currently applicators used for PDT of the anal cavity only facilitate the delivery of light to either the perianal or intra-anal region and do not facilitate probes to monitor explicit and/or implicit parameters to provide an insight of the relationship between the treatment and tissue response in situ. Thus, it would be advantageous to dynamically monitor explicit and implicit parameters during perianal or intra-anal PDT treatment in order to aid in optimizing and standardizing PDT therapy.

Due to the disadvantages of conventional treatment modalities and previous PDT therapies of perianal and intra-anal AIN III, there is a need to provide dynamically enhanced PDT treatments for safe and improved clinical PDT treatment protocols.

OBJECTIVES AND BRIEF SUMMARY OF THE INVENTION

It is an objective of present invention to provide PDT methods, devices and compositions for treatment of abnormal cell growth in anal tissue such as perianal and intra-anal grade 3 Anal Intraepithelial Neoplasia (AIN III).

Yet another objective of present invention is to provide enhanced PDT treatments for safe and improved colorectal PDT treatment protocols by dynamically monitoring explicit and implicit parameters during perianal or intra-anal PDT treatments.

Still another objective of present invention is to provide devices for enhanced intra-anal PDT treatment for severe dysplasia such as AIN III, providing means for enhanced delivery of electromagnetic radiation.

A further objective is to provide compositions containing hydrophobic photosensitizers for colorectal photodynamic therapy for the treatment of unwanted cells and tissues of the intra-anal and of the perianal region.

Briefly stated, dynamic colorectal PDT methods, devices and photosensitizer compositions to treat abnormal cell growth in anal tissue such as perianal and intra-anal intraepithelial neoplasia grade III are presented. A dynamic colorectal PDT method comprises the steps of administering topically, intravenously or orally a photosensitizer composition; irradiating; and monitoring treatment parameters before, during and/or after irradiation. A photosensitizer composition comprises Temoporfin (m-THPC) and excipients and carriers, appropriate for the method of application. An applicator is provided for colorectal PDT treatments to enhance irradiation delivery and monitor treatment parameters. Preferably, said applicator is made of a material which is used to monitor the fluence rate at the same time as doing optical spectroscopy. Measurement probe devices are provided for monitoring PDT treatment parameters in vivo. A device for colorectal PDT treatment is also provided, comprising a laser radiation source operating at about 400 and 800 nm; an excitation laser radiation source operating at about 650 nm for fluorescence measurements; a multichannel dosimetry device; a long pass filter; waveguides and measurement probes.

The above, and other objects, features and advantages of the present invention will become apparent from the following description read in conjunction with the accompanying drawings, in which like reference numbers in different drawings designate the same elements.

DETAILED DESCRIPTION OF PREFERRED EMBODIMENTS

Figure 1:
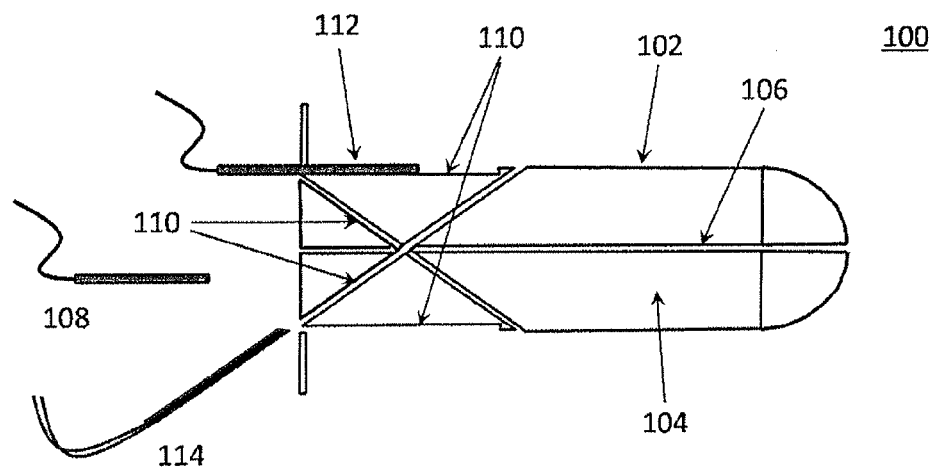
FIG. 1 illustrates a schematic longitudinal cross section of a preferred embodiment showing the location of all optical fiber conduits in the applicator.

The present invention provides PDT methods, devices and compositions containing hydrophobic photosensitizers for treatment of abnormal cell growth in anal tissue such as perianal and intra-anal grade 3 anal intraepithelial neoplasia (AIN III). A main advantage of present invention is that it provides a safer and enhanced colorectal PDT treatment of perianal and intra-anal AIN III due to the possibility of monitoring in situ implicit and explicit parameters which allow a better control of PDT treatment parameters. By monitoring implicit or explicit parameters such as fluence, fluence rate, fluorescence, photosensitizer concentration, tissue oxygenation, saturation and blood volume, a more precise relationship between PDT treatment parameters and tissue response in situ can be established. Additionally, a safe and homogenous electromagnetic radiation delivery is obtained by using the devices disclosed in the present invention.

In one embodiment, a colorectal PDT method for treatment of peri-anal and intra-anal AIN III comprises the steps of: 1) administering an effective dose of a photosensitizer composition; 2) placing at least one measurement probe and at least one treatment waveguide in treatment site; 3) irradiating said treatment site; and 4) monitoring treatment parameters before, during and/or after irradiation. Before the administration of a photosensitizer composition and after irradiation the patient is maintained under subdued light conditions for a predetermined time interval in order to avoid undesired and uncontrolled photosensitizer activation. The time interval between the administration of the photosensitizer composition and the irradiation step will generally depend on the photosensitizer composition, dose, patient condition and means of administration (topical, oral or involving any part of the gastrointestinal tract, or intravenous administration). In the case of intra-anal AIN III treatment, an applicator disclosed in present invention is inserted in treatment area in order to access and make contact with the unfolded and nearly unreachable unhealthy mucosa. At least one treatment waveguide is an optical fiber selected from the group consisting of radial fibers, linear diffusers, balloon fibers and similar, providing that the tip of the optical fiber ensures a proper and efficient delivery of radiation energy to the target tissue. Measurement probes include, but are not limited to passive and/or active probes. In a preferred embodiment, the measurement probe is a device disclosed in present invention, defined as a fluorescence differential path length spectroscopic (FDPS) probe. By placing the treatment waveguide(s) and the measurement probe(s) in the anal cavity with the aid of present invention applicator there is scarcely or no risk of damage or perforation of the mucosa. In the case of intra-anal AIN III treatment, an occluding cloth is placed at the base of present invention applicator to prevent irradiation of normal skin around the perianal region. For perianal AIN III treatment the irradiation region is carefully delimitated with the aid of dark materials such as black paraffin or similar. The preferred parameters monitored include but are not limited to fluence, fluence rate, fluorescence, photosensitizer concentration, tissue oxygenation, saturation and blood volume. The great advantage of measuring the fluence rate in vivo at the anal wall is that the irradiation dose can be accurately controlled while the treatment is performed, so possible overtreatment of tissue is avoided, which can possibly lead to negative side effects such as perforations or anal dysfunctions. Preferably, fluence rate is measured in vivo at the anal wall at two opposite locations. Once the required dose is achieved the irradiation step is stopped and the applicator, waveguide(s) and measurement probe(s) are removed from the treatment site. A significant advantage of the present colorectal PDT method is that it allows therapeutic irradiation of the whole surface of treatment site in a single treatment session, while other employed treatment devices/methods have shown that is difficult to determine exactly where to treat for AIN III in the anal cavity, and thus under-treat some tissue and overtreat other tissue.

In a preferred embodiment, the photosensitizer composition includes tetrapyrrole and their derivatives as photosensitizer and appropriate excipients and carriers, depending on the pharmaceutical dosage form adopted according to the route of administration selected. Preferably, the photosensitizer is selected from the group consisting of porphyrins, chlorins, pheophorbides and bacteriopheophorbides. In a most preferred embodiment the photosensitizer exogenously administered is Temoporfin (m-THPC).

One disadvantage of currently applicators used for PDT for the anal cavity is that they only facilitate the delivery of radiation to the intra-anal region; and do not facilitate probes to monitor explicit parameters such as fluence, fluence rate, photosensitizer concentration, tissue oxygenation, and/or implicit parameters such as fluorescence photobleaching. Since the deposited PDT dose depends on the concentration of photosensitizer, irradiation treatment parameters and the tissue oxygen concentration, monitoring these parameters can give information not only on delivered PDT dose but also provide an insight to the relationship between PDT dose and tissue response. For this reason the applicator of present invention provides means to monitor explicit and implicit parameters which aid in optimizing and standardizing PDT treatments and offers enhanced and safer PDT procedures. An applicator for colorectal PDT treatment of present invention comprises a hollowed-shape element with at least one center conduit; at least two conduits placed opposite each other at the surface of said hollowed-shaped element parallel to said center conduit; and at least two conduits with a slope. Additionally, adjustable spacers may be placed in the conduits to prevent damage to the anal mucosa by inserting measurement probes. Preferably, measurement probes are fluorescence differential path length spectroscopy (FDPS) measurement probes. In addition, the applicator of present invention is preferably made of a material which could be used to monitor the fluence rate at the same time as doing optical spectroscopy. Preferably, said material is a polymeric material which has a Raman peak from a C—H stretch that could usually be identified as an amide group. In a preferred embodiment depicted in FIG. 1, applicator 100, which delivers radiation and monitors treatment parameters for PDT treatments of intra-anal AIN III, comprises hollowed cylinder with the shape of a clinical anoscope 102 which is a hollowed-shape element preferably made of plastic, medical grade silicone 104 to fill in clinical anoscope 102; at least one center conduit 106 to place at least one treatment waveguide, more preferably, treatment optical fiber 108 and additional measurement conduits 110 to place optical fiber probes. Preferably, there are at least four additional measurement conduits 110. A pair of additional measurement conduits 110 are placed opposite each other at the surface of the applicator and parallel to center conduit 106 in order to place linear diffusers 112 of appropriate diffusing length based on the size of the lesion to measure fluence rate and fluence at the anal mucosa; and another pair of additional measurement conduits 110 are under a slope of 35 degrees to facilitate contact of FDPS measurement probes 200 with the anal wall. Preferably, the distal ends of FDPS measurement probes 200 are polished under an angle of 35 degrees to minimize specular reflection between the probe-tissue interface. Adjustable spacers may be placed on the FDPS measurement probes 200 to prevent damage to the anal mucosa from potentially inserting the FDPS measurement probes 200 too far. With this configuration, the radiation distribution along the applicator is homogeneous for the length of diffuser used for treatment. Furthermore, due to the existence of measurement probes and their location in different positions it is possible to provide a safer PDT treatment by monitoring in situ treatment parameters that allows delivering the appropriate PDT light dose while minimizing damage to surrounding healthy tissue. Additionally, the applicator of present invention does not influence, minimally or slightly influences the fluence rate profile of the treatment waveguide, embodied as a treatment optical fiber.

Figure 2:
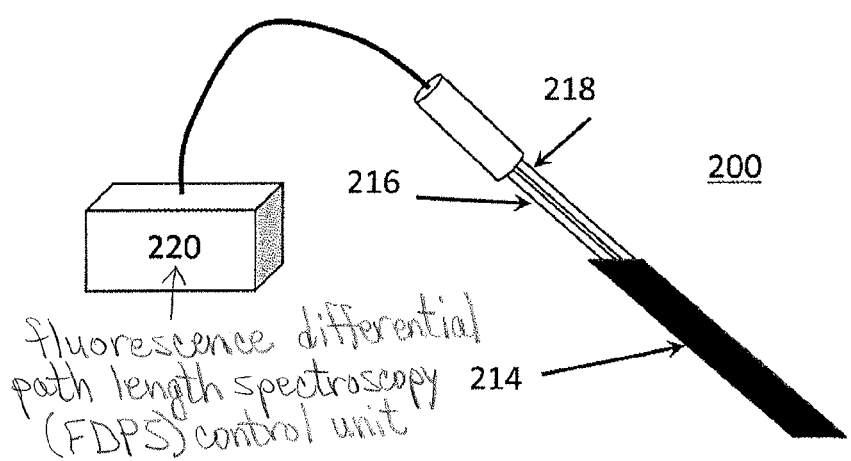
FIG. 2 shows another preferred embodiment of a device for PDT treatment of perianal and intra-anal AIN III.

Present invention also provides measurement probe devices, in order to monitor implicit and explicit PDT treatment parameters, comprising a hollow element of medical-grade metal; at least two waveguides, placed at a predetermined core-to-core distance of said hollow element of medical-grade metal; and a fluorescence differential path length spectroscopy control unit. In this disclosure measurement probe devices are also called FDPS measurement probes due to the control unit used to process a range of treatment parameters. FIG. 2 shows schematically an embodiment of FDPS measurement probe 200 comprising stainless steel needle 214 which embodies a hollow element of medical-grade metal, containing two waveguides, radiation delivery and collection optical fiber 216 and collection optical fiber 218, both placed at a determined core-to-core distance of the needle. Stainless steel needle 214, radiation delivery and collection optical fiber 216 and collection optical fiber 218 are polished under an angle of 35 degrees to minimize specular reflection at the probe-tissue interface. This angle was chosen to optimize probe-tissue contact in the current measurement/treatment geometry in combination with the used treatment applicator, however, other polished angles can also be chosen depending on the measurement/treatment geometry and the treatment applicator used. Radiation delivery and collection optical fiber 216 and collection optical fiber 218 are connected to fluorescence differential path length spectroscopy (FDPS) control unit 220.

Figure 3:
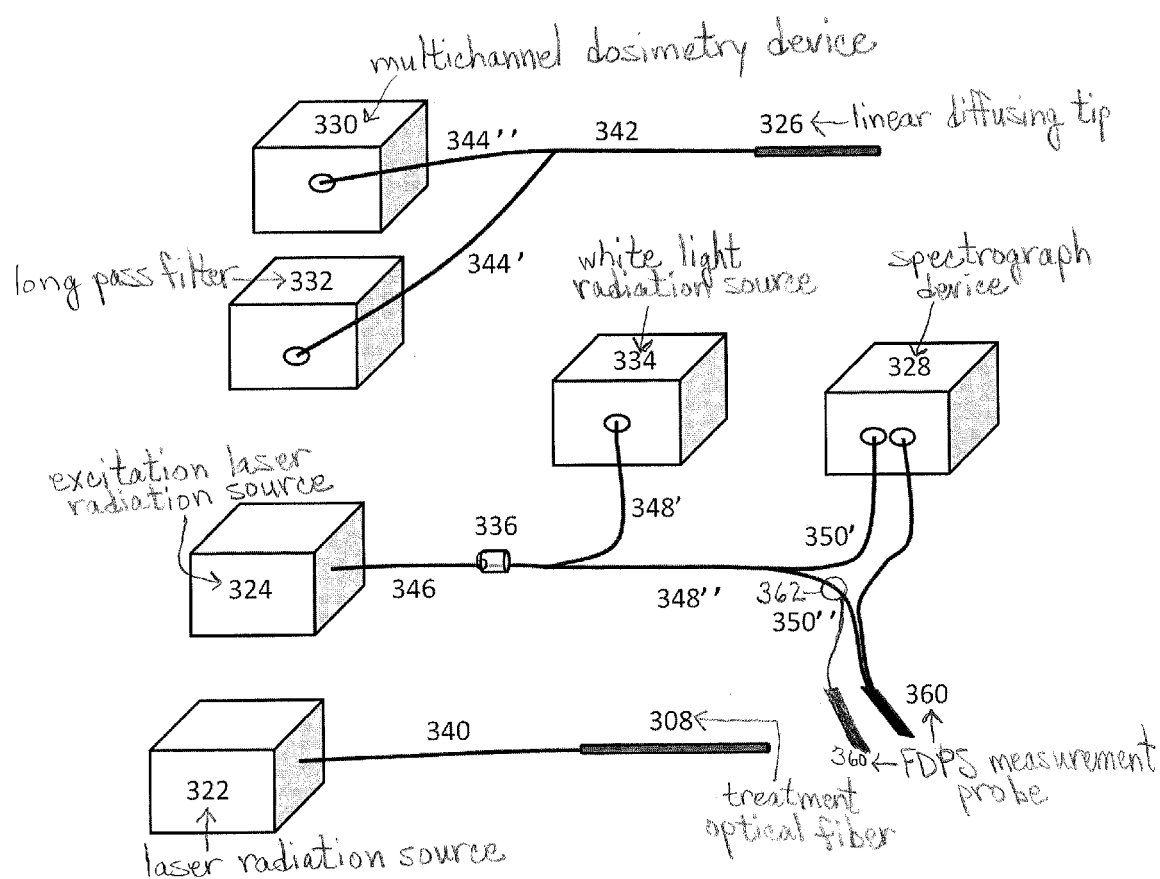
FIG. 3 shows a schematic view of an embodiment of fluorescence differential path length spectroscopy (FDPS) measurement probes of present invention.

In another embodiment, a device for colorectal PDT treatment comprises at least two radiation sources, a multichannel dosimetry device, a long pass filter, waveguides and FDPS measurement probes. Preferably, waveguides are optical fibers selected from the group consisting of radial optical fibers, linear diffusers, balloon optical fibers, bifurcated optical fibers and combinations of them. Radiation sources include coherent and incoherent radiation sources such as laser radiation sources, light emitting diode sources, lamp radiation source (incandescent, xenon arc and metal halide lamps), whose output is or can be regulated within a preselected spectral window. FIG. 3 describes a preferred embodiment of the present invention, a device comprising radiation sources: laser radiation source 322, excitation laser radiation source 324 and white light radiation source 334; waveguides as treatment optical fiber 308, linear diffusing tip 326, optical fibers and bifurcated optical fibers; spectrograph device 328; multichannel dosimetry device 330; long pass filter 332; shutter 336; and FDPS measurement probe 360. Laser radiation source 322 preferably operates at about 400 and at about 800 nm. This range is preferred because within these wavelengths, laser radiation energy activates the photosensitizer exogenously administered, and; depending on the wavelength, different penetration depths can be achieved. Excitation laser radiation source 324 is preferably a 650 nm diode laser for fluorescence measurements and delivers laser radiation to FDPS measurement probe 360. If more than one FDPS measurement probe 360 is used, as is usually the case, a laser beam splitter 362 is set at the excitation laser radiation source output to deliver laser radiation to multiple FDPS measurement probes 360. Additionally, shutter 336 is placed in laser radiation path to control the excitation laser radiation for each FDPS measurement probe 360. The proximal end of optical fiber 340 is connected to laser radiation source 322 and the distal end of optical fiber 340 is coupled to treatment optical fiber 308.

Linear diffusing tip 326 is connected to the proximal end of optical fiber 342. The distal end of optical fiber 342 is coupled to the proximal end of bifurcated optical fiber 344. The distal end of bifurcated optical fiber 344" is connected to multichannel dosimetry device 330. The distal end of bifurcated optical fiber 344' is connected to long pass filter 332.

Excitation laser radiation source 324 is connected to the proximal end of optical fiber 346. Shutter 336 is placed in laser radiation path to control the excitation laser radiation. The distal end of optical fiber 346 is coupled to the proximal end of bifurcated optical fiber 348. The distal end of bifurcated optical fiber 348' is coupled to white light radiation source 334 for FDPS measurements and bifurcated optical fiber 348" is coupled to the proximal end of bifurcated optical fiber 350. The distal end of bifurcated optical fiber 350' is connected to spectrograph device 328. The distal end of bifurcated optical fiber 350" is coupled to the radiation delivery and collection optical fiber of FDPS measurement probe 360.

In another embodiment, light dosimetry and long wavelength fluorescence are measured with linear diffusing tips of 1 cm or isotropic tips at the distal end of a 400 micron optical fiber. The other end of the optical fiber is split using a 200/400 micron bifurcated fiber. The 200 micron arm of the bifurcated fiber is coupled into a modular based multichannel dosimetry device. The 400 micron arm is coupled into a long pass filtered, channel of a two-channel spectrograph, which blocks light less than 690 nm wavelengths).

Apart from measuring treatment parameters in situ, in one embodiment a data processing unit can be used in order to manage fluorescence spectroscopy data, fluorescence differential path-length spectroscopy data and signals measured with measurement probes. In one embodiment, long wavelength fluorescence spectra are analyzed as a linear combination of basis spectra using a singular value decomposition (SVD) algorithm. The fluorescence can be described by a combination of autofluorescence and m-THPC fluorescence, when this is the photosensitizer used. The autofluorescence basis-spectrum can be defined as the average of acquired spectra measured in a patient before m-THPC was administered. The m-THPC basis-spectrum can be defined as the average of spectra acquired in m-THPC administered patients with subtraction of the autofluorescence signal. In the case of fluorescence differential path-length spectroscopy data, differential fluorescence spectra can be analyzed using the same SVD as for the long wavelength fluorescence with the addition of a third component. The differential fluorescence spectra contain contribution from the therapeutic laser. The residual laser light in the fluorescence spectra can be described by a Gaussian, peak at 648 nm width 12.3 nm. The autofluorescence basis-spectrum is defined as the average of spectra acquired in a patient before m-THPC was administered and the m-THPC basis-spectrum is defined as the average of spectra acquired in m-THPC administered patients with subtraction of the autofluorescence and residual laser light. Additionally, the differential reflectance signal is used to obtain values on saturation and blood volume.

The present invention is further illustrated by the following examples, but is not limited thereby.

Example 1

Patients with biopsy proven clinical intra-anal AIN III were treated. Forty-eight hours before illumination patients were administered with 0.075 mg/kg intravenous m-THPC (Biolitec AG, Jena, Germany). During the 48 hours between administration and therapeutic illumination, patients were sent home with a lux meter (Voltcraft, Oldenzaal, the Netherlands) and with instructions to remain under subdued light conditions.

At the time of treatment a special designed applicator of present invention was placed in the anal cavity. During treatment this applicator contains the treatment fiber, 5 cm linear diffuser (CeramOptec, Jena, Germany), and four fiber optic probes, 1 cm linear diffusers (CeramOptec, Jena, Germany) and FDPS probes, to monitor fluence (rate), fluorescence, saturation and blood volume during therapeutic illumination. The applicator was placed with the treatment fiber and the two linear diffusers to measure fluence (rate). After placement of the applicator, FDPS probes were placed to prevent damage or perforation of the anal mucosa upon insertion due to the steel casing of these probes. Finally an occluding cloth was applied at the base of the applicator to prevent illumination of normal skin around the perianal region. Before illumination, saturation and blood volume were measured to acquire pre-illumination values. Based on the size of the lesion, a linear diffuser of appropriate length was chosen to insert in the treatment channel of the applicator. The fluence rate was measured in vivo at the anal wall and set to 45-50 $mWcm^{-2}$ which took on average 10 seconds. Illumination was stopped when the desired dose, measured in vivo at the anal wall, had been delivered. The delivered dose was between 10 and 17 $Jcm^{-2}$. Fluence (rate) was measured at two opposite locations. Treatment was stopped as soon as one of the probes indicated that the desired fluence was reached, to prevent possible overtreatment of tissue which could possibly lead to negative side effects, such as perforations or anal dysfunction. After illumination the applicator was removed and as a precaution the patient stayed in overnight to monitor response. The acute response and the side effects associated by PDT were assessed in the days following therapy.

Example 2

Figure 4:
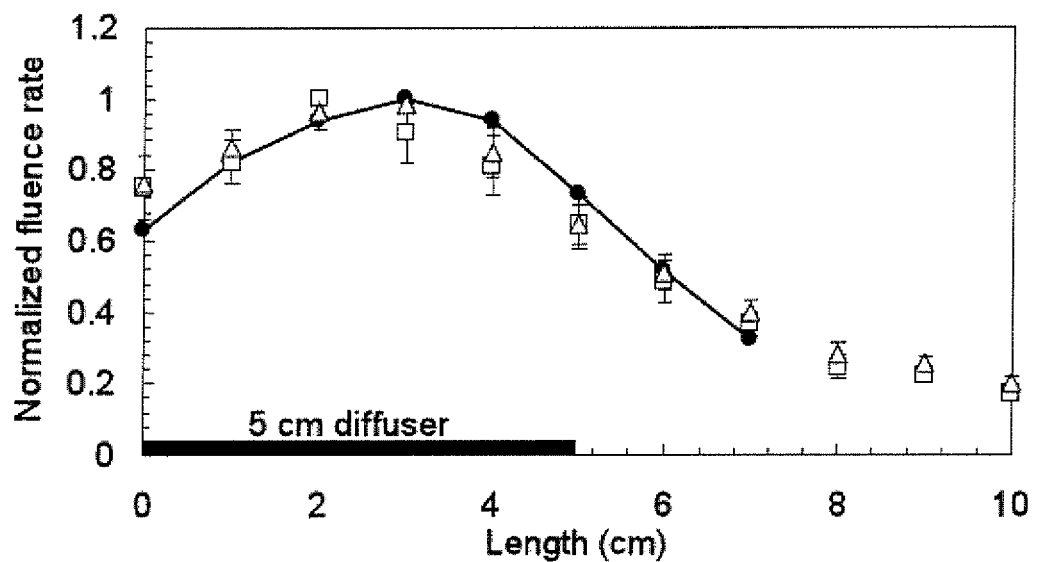
FIG. 4 shows the normalized fluence rate as a function of length for measurements along the applicator with all optical fibers at their correct position; in which open squares correspond to measurements done on the side where the measurement optical fibers were located and open triangles on a side where no measurement optical fibers were located. The solid line represents the fluence rate profile of the linear diffuser used for treatment (i.e. measured outside the applicator).

The radiation distribution of the applicator was investigated by measuring along the applicator when immersed in scattering phantom (intralipid diluted in water), with all measurement and treatment optical fibers inserted. FIG. 4 shows the normalized measured fluence rate as function of distance along the applicator, with the linear diffuser located in the center channel of the applicator. Fluence rate was measured in a longitudinal direction along the applicator at two sides, one side where no measurement probes were located (open triangles) and one side where measurement probes were located (open squares). The thick black line represents the profile of the linear diffuser itself. The two fluence rate profiles measured at the surface of the applicator at two different sides both overlap with the fluence rate profile of the linear diffuser on itself (i.e. profile of the linear diffuser measured outside the applicator in the same phantom). Thus, it could be shown that the applicator has little influence on the fluence rate profile of the linear diffuser used for delivering the therapeutic radiation.

Figure 5:
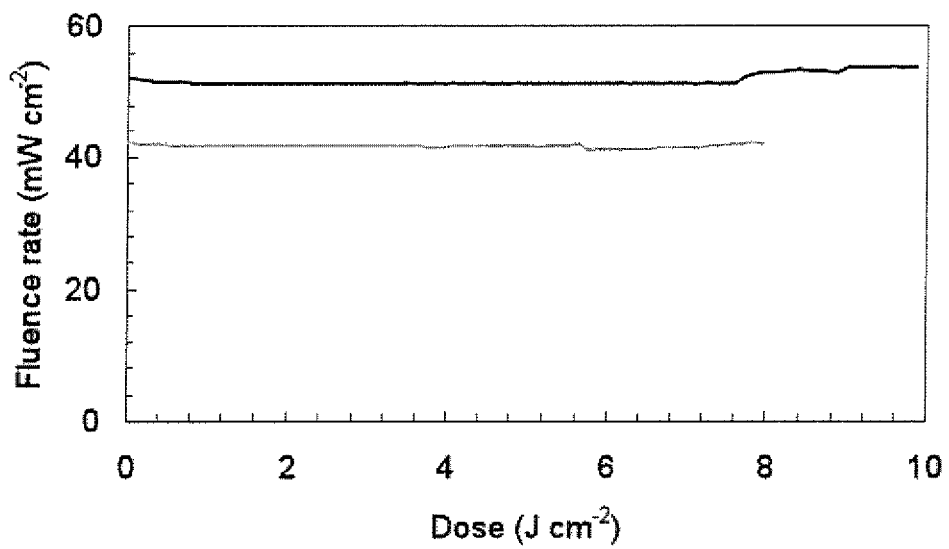
FIG. 5 shows the measured fluence rate as a function of delivered irradiation dose measured in situ at two locations (black and gray lines) in a single patient.

Additionally, radiation dosimetry was also assessed. FIG. 5 shows the measured fluence rate as a function of delivered radiation dose for two opposite locations (black and gray lines) in a single patient. In different patients, and different locations, the fluence rate was found to be constant, or gradually increasing or decreasing during therapeutic irradiation. However the amounts of increase or decrease in fluence rate were within 10%. At one location in a single patient a decrease in fluence rate of 17% was observed.

Example 3

Figure 6:
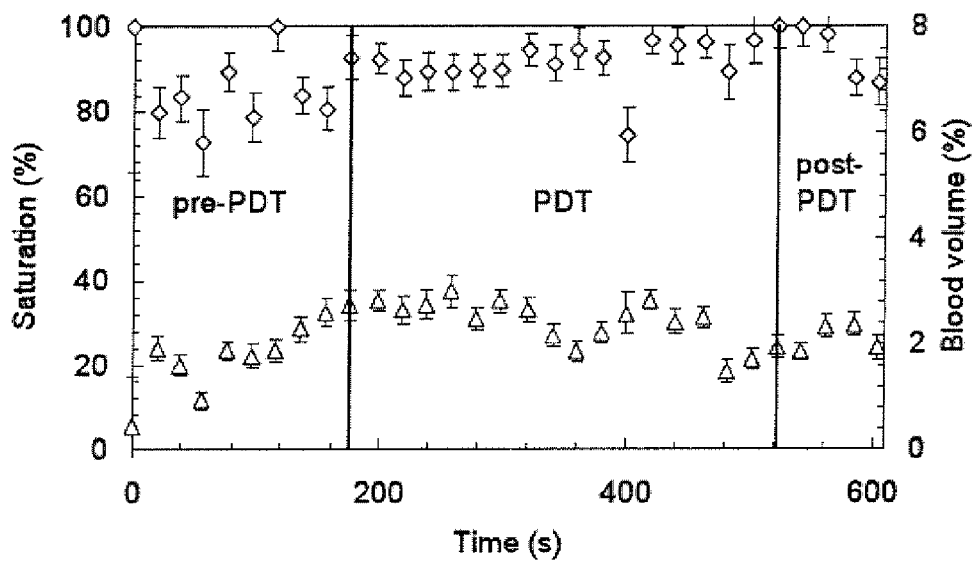
FIG. 6 shows saturation (open diamonds) and blood volume (open triangles) as a function of time measured during the course of treatment in a patient with a delivered dose of 17 $Jcm^{-2}$. The vertical lines indicate start and end of therapeutic illumination.
Figure 7:
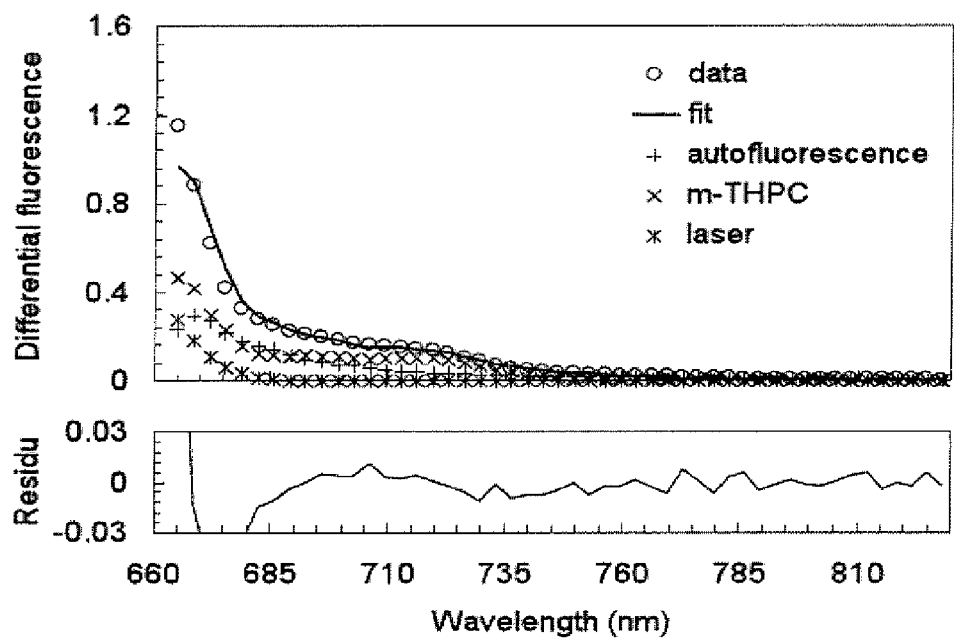
FIG. 7 shows a differential fluorescence spectrum (open circles) with its fit (solid line) and residual, and the individual components.

One of the advantages of FDPS is that it allows monitoring oxygen saturation in blood (ratio between oxy- and deoxy-hemoglobin), blood volume and fluorescence over the same volume. FIG. 6 shows the measured saturation (open diamonds) and blood volume (open triangles) at a single location during the course of treatment, i.e. before, during, and after therapeutic illumination. The vertical lines indicate start and end of therapeutic irradiation. This corresponds to a particular patient who received a radiation dose of 17 J·cm$^{-2}$. The saturation shows to be relatively constant during illumination for this patient while the blood volume shows oscillating behavior. FIG. 7 shows the fit and components of a measured differential fluorescence spectrum and its residual. The shallow peak at 720 nm is due to the presence of m-THPC.

Figure 8:
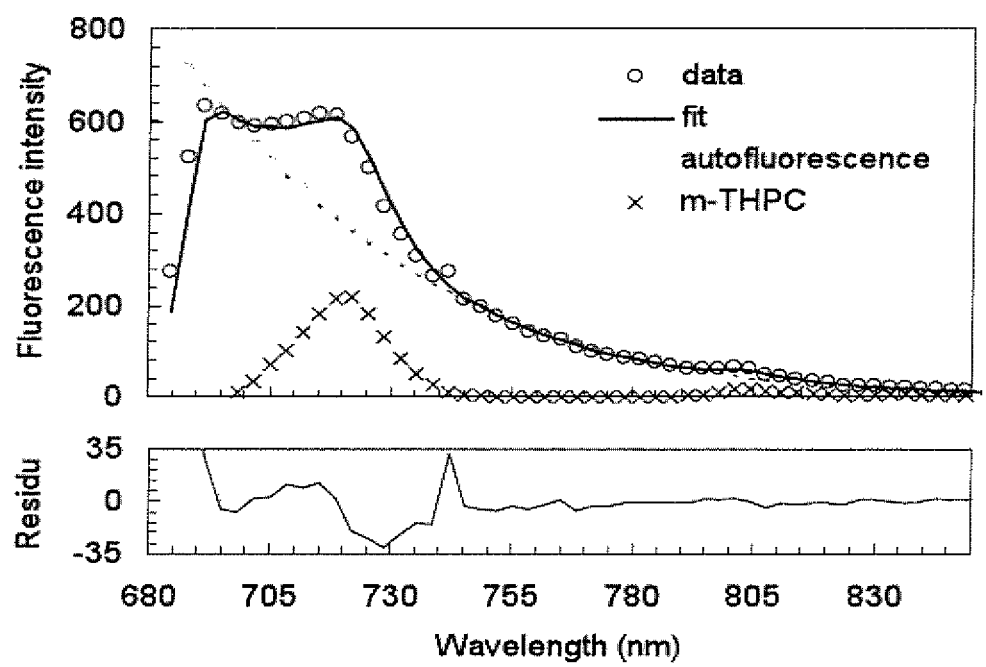
FIG. 8 shows a long wavelength fluorescence spectrum acquired by a 1 cm linear diffuser (open circles), used for monitoring fluence (rate) and fluorescence, with its fit (solid line) and residual, and the individual components.

Long wavelength fluorescence can also be measured. FIG. 8 shows a fluorescence spectrum and its fit with the individual components and the residual, acquired with the 1 cm linear diffusers on the opposite sides of the applicator. In contrast to the differential fluorescence, the long wavelength fluorescence measured by the linear diffusers interrogates an unknown but larger volume than the FDPS signal. Since a different optical filter was used in this setup it was not necessary to have a component for the laser radiation.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A medical device for colorectal PDT treatment comprising;
   a) at least one radiation source;
   b) a multichannel dosimetry device;
   c) a long pass filter;
   d) an applicator having a distal end and a proximal end, being sized and adapted for the distal end to be inserted intra-anally and comprising: 1) a center conduit extending along a longitudinal axis of the applicator, 2) at least one measurement conduit sloped with respect to the center conduit such that the distal end of a probe inserted into the proximal end of the measurement conduit would point away from the distal end of the center conduit, and 3) at least one measurement conduit at the surface of the applicator parallel to the center conduit;
   e) at least one waveguide for insertion into the proximal end of the center conduit of the applicator;
   f) at least one sloped measurement probe for insertion into the proximal end of the at least one sloped measurement conduit; and
   g) at least one surface measurement probe for insertion into the proximal end of the at least one measurement conduit at the surface of the applicator.

2. The device for colorectal PDT treatments according to claim 1, wherein said radiation source is a coherent or incoherent radiation source selected from the group consisting of lasers, white light sources, light emitting diodes, lamps, and a combination of these whose output can be regulated within a preselected spectral window.

3. The device for colorectal PDT treatments according to claim 1, wherein said at least one waveguide is an optical fiber selected from the group consisting of radial optical fibers, linear diffusers, balloon optical fibers, bifurcated optical fibers and combination of these.

4. The device for colorectal PDT treatments according to claim 1, wherein said at least one radiation source is a laser radiation source operating at 400 to 800 nm optically connected to said at least one waveguide for insertion into the center conduit of the applicator.

5. The device for colorectal PDT treatments according to claim 1, wherein said at least one radiation source is an excitation laser radiation source operating at 650 nm for fluorescence measurements optically connected to said at least one surface measurement probe.

6. The device for colorectal PDT treatments according to claim 5, wherein said excitation laser radiation source is used with one or more laser beam splitters.

7. The device for colorectal PDT treatments according to claim 5, wherein a shutter is placed in the laser radiation path to control the excitation laser radiation for the at least one surface measurement probe.

8. The device for colorectal PDT treatments according to claim 1, wherein a data processing unit is used to manage fluorescence spectroscopy data, fluorescence differential path-length spectroscopy data, and signals measured with measurement probes.

9. The medical device for colorectal treatment according to claim 1 which comprises two measurement conduits sloped with respect to the center conduit and two measurement conduits opposite each other at the surface of the applicator.

10. The medical device for colorectal PDT treatment according to claim 9, wherein adjustable spacers are placed in the sloped conduits to prevent damage to the anal mucosa by inserting measurement probes.

11. The medical device for colorectal PDT treatment according to claim 9, wherein the slope of each of said sloped conduits from the longitudinal axis of the applicator is 35 degrees.

12. The medical device for colorectal PDT treatment according to claim 9, wherein said applicator further comprises a material which is used to monitor the fluence rate at the same time as doing optical spectroscopy.

13. The medical device for colorectal PDT treatment according to claim 12, wherein said material is a polymeric material which has a Raman peak from a C—H stretch/an amide group.

14. The device for colorectal PDT treatment according to claim 1, wherein said sloped measurement probe comprises:
   i) a hollow element of medical-grade metal;
   ii) at least two waveguides, placed at a determined core-to-core distance of said hollow element of medical-grade metal; and
   iii) a fluorescence differential path length spectroscopy control unit;
wherein said measurement probe's outputs are processed with the aid of a fluorescence differential path length spectroscopy control unit.

15. The medical device for colorectal PDT treatment according to claim 14 wherein said waveguides have a slope at distal tips.

16. The medical device for colorectal PDT treatment according to claim 15, wherein said slope at the tip is about 35 degrees.

17. The medical device for colorectal PDT treatment according to claim 14, wherein at least one of said waveguides is a radiation delivery and radiation collector optical fiber.

18. The medical device for colorectal PDT treatment according to claim 14, wherein said hollow element of medical-grade metal is a stainless steel needle.

19. The medical device for colorectal PDT treatment according to claim 14, wherein at least one of said waveguides is a radiation collector optical fiber.

* * * * *